(12) United States Patent
Gallenkamp et al.

(10) Patent No.: US 10,647,667 B2
(45) Date of Patent: May 12, 2020

(54) METHOD FOR PREPARING 3-SUBSTITUTED 2-VINYLPHENYL SULFONATES

(71) Applicant: BAYER CROPSCIENCE AKTIENGESELLSCHAFT, Monheim am Rhein (DE)

(72) Inventors: Daniel Gallenkamp, Wuppertal (DE); Mark James Ford, Wiesbach-Breckenheim (DE); Dirk Brohm, Mettmann (DE); Florian Erver, Wiesbaden (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/466,273

(22) PCT Filed: Nov. 28, 2017

(86) PCT No.: PCT/EP2017/080624
§ 371 (c)(1),
(2) Date: Jun. 3, 2019

(87) PCT Pub. No.: WO2018/104105
PCT Pub. Date: Jun. 14, 2018

(65) Prior Publication Data
US 2020/0071267 A1    Mar. 5, 2020

(30) Foreign Application Priority Data

Dec. 5, 2016 (EP) ..................................... 16202158

(51) Int. Cl.
*C07C 303/28* (2006.01)
*C07D 319/08* (2006.01)
*C07C 37/00* (2006.01)

(52) U.S. Cl.
CPC .......... *C07C 303/28* (2013.01); *C07C 37/002* (2013.01); *C07D 319/08* (2013.01)

(58) Field of Classification Search
CPC .... C07C 303/28; C07C 37/002; C07D 319/08
See application file for complete search history.

(56) References Cited

U.S. PATENT DOCUMENTS

| | | |
|---|---|---|
| 5,424,460 A | 6/1995 | Duhamel et al. |
| 8,524,743 B2 | 9/2013 | Cristau et al. |
| 9,167,821 B2 | 10/2015 | Cristau et al. |
| 9,247,748 B2 | 2/2016 | Cristau et al. |
| 9,717,243 B2 | 8/2017 | Hillebrand et al. |
| 9,751,871 B2 | 9/2017 | Cristau et al. |
| 10,160,707 B2 | 12/2018 | Erver et al. |
| 2011/0224257 A1 | 9/2011 | Cristau et al. |
| 2014/0057945 A1 | 2/2014 | Cristau et al. |
| 2015/0065541 A1 | 3/2015 | Cristau et al. |
| 2016/0135461 A1 | 5/2016 | Hillebrand et al. |
| 2016/0214970 A1 | 7/2016 | Cristau et al. |
| 2017/0101359 A1 | 4/2017 | Erver et al. |
| 2018/0079717 A1 | 3/2018 | Bruchner et al. |

FOREIGN PATENT DOCUMENTS

| | | |
|---|---|---|
| EP | 0511036 A1 | 10/1992 |
| WO | 2011076699 A1 | 6/2011 |
| WO | 2012087229 A1 | 6/2012 |
| WO | 2014206896 A1 | 12/2014 |
| WO | 2015189114 A1 | 12/2015 |
| WO | 2016139161 A1 | 9/2016 |

OTHER PUBLICATIONS

International Search Report for PCT/EP2017/080624 filed on Dec. 15, 2017.
Yamaguchi M et al: "Ortho-Vinylation Reaction of Phenols With Ethyne", The Journal of Organic Chemistry, American Chemical Society ETC, Jan. 1, 1998, pp. 7298-7305, vol. 63, No. 21.

*Primary Examiner* — Rosalynd A Keys
(74) *Attorney, Agent, or Firm* — McBee Moore & Vanik IP, LLC

(57) ABSTRACT

The present invention relates to a method for preparing 3-substituted 2-vinylphenyl sulfonates.

15 Claims, No Drawings

METHOD FOR PREPARING 3-SUBSTITUTED 2-VINYLPHENYL SULFONATES

CROSS-REFERENCE TO RELATED APPLICATIONS

This application is the National Stage entry of International Application No. PCT/EP2017/080624, filed 28 Nov. 2017, which claims priority to European Patent Application No. 16202158.8, filed 5 Dec. 2016.

BACKGROUND

Field

The present invention relates to a method for preparing 3-substituted 2-vinylphenyl sulfonates, particularly 3-chloro-2-vinylphenyl sulfonates.

Description of Related Art 3-substituted 2-vinylphenyl sulfonates are important intermediates for preparing agrochemically active compounds (see e.g. WO 2011/076699 or WO 2014/206896).

The 3-substituted 2-vinylphenyl sulfonates are typically prepared by reacting the corresponding 3-substituted 2-vinylphenols with an aryl- or alkylsulfonyl chloride. For instance, the preparation of 3-chloro-2-vinylphenol via tetrachlorocyclohexanone and trichloro-1,3,3-vinyl-2-oxa-7-bicyclo-[4.1.0]heptane as intermediates is known from EP 0511036 B1. Disadvantages of the method are a low overall yield and a low atom economy.

WO 2016/139161 describes the preparation of 3-chloro-2-vinylphenol in a two-stage process by reacting 2-chloro-6-hydroxybenzaldehyde with MeMgBr to give 3-chloro-2-(1-hydroxyethyl)phenol and subsequent elimination of water. The 2-chloro-6-hydroxybenzaldehyde is prepared from 3-chloro-2-(dichloromethyl)phenyl trichloroacetate. However, with regard to atom economy, this method is still worthy of improvement. An alternative method for preparing 2-chloro-6-hydroxybenzaldehyde is known from WO 2012/087229. Owing to the reagents used, such as DMSO as solvent unsuitable for technical use, and the low yield, this method is also worthy of improvement.

SUMMARY

The object of the invention, therefore, was to provide an improved method for preparing 3-substituted 2-vinylphenyl sulfonates. The method should allow the desired product to be prepared in high yield with few stages and purification steps and maximum atom economy.

This object was achieved by a method for preparing 3-substituted 2-vinylphenyl sulfonates of the formula (I):

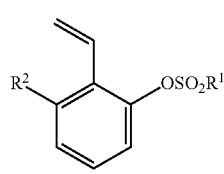

(I)

in which
$R^1$ is $C_1$-$C_6$-alkyl, phenyl, 4-methylphenyl or benzyl, and
$R^2$ is halogen or methyl,
characterized in that
(a) a compound of the formula (II)

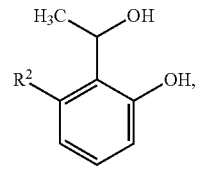

(II)

is reacted with an activator selected from the group consisting of thionyl chloride, phosgene, diphosgene, triphosgene, thiophosgene and chloroformic esters, in the presence of a base to give a compound of the formula (III)

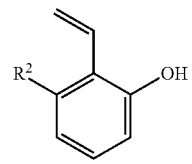

(III)

and
(b) the compound of the formula (III) is reacted in the presence of a base with a compound of the formula (IV)

$R^1$—$SO_2$—$R^3$ (IV), where $R^3$ is F, Cl, Br or $OSO_2R^1$ and $R^1$ is as defined in formula (I),
to give the 3-substituted 2-vinylphenyl sulfonate of the formula (I).

DETAILED DESCRIPTION OF A PREFERRED EMBODIMENT

It has been found, surprisingly, that 3-substituted 2-vinylphenyl sulfonates may be prepared from the corresponding 3-substituted 2-(1-hydroxyethyl)phenols with the aid of an activator, such as phosgene or thionyl chloride for example, in high yield and without the necessity of isolating intermediates.

In comparison to the method known from WO 2016/139161, the method according to the invention has the advantage that (i) a lower amount of compound of the formula (IV) has to be used and thionyl chloride or phosgene are significantly cheaper compared to compounds of the formula (IV), (ii) as waste products in step (a) only one equivalent of gaseous substances ($SO_2$, $CO_2$) is formed instead of one equivalent of methanesulfonic acid and (iii) an improved yield is achieved. In a preferred variant of the method according to the invention, the base can also be recycled. Due to these advantages, the method according to the invention is particularly suitable for use on an industrial scale.

The method according to the invention is preferably carried out as a one-pot process. In accordance with the invention, this signifies that steps (a) and (b) are carried out without isolating intermediate (III).

The method according to the invention is shown in Scheme 1.

Scheme 1

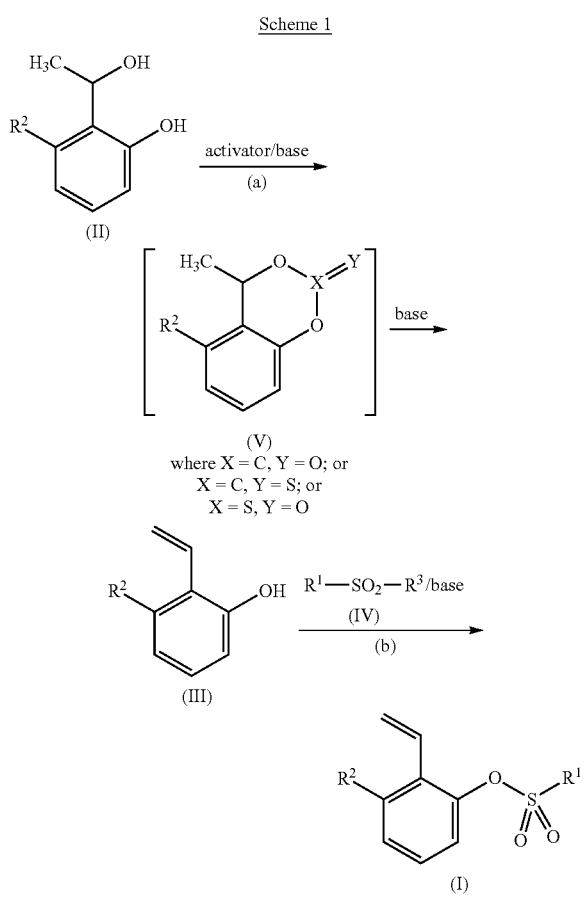

(V)
where X = C, Y = O; or
X = C, Y = S; or
X = S, Y = O

It has been found that the conversion of the compound of the formula (II) in the presence of the activator and the base proceeds via the cyclic intermediate (V) to give the compound of the formula (III). Then, by elimination of O=X=Y from the cyclic intermediate (V), the compound of the formula (III) is formed.

In accordance with the invention, the compound of the formula (III) is then reacted in the presence of a base with a compound of the formula (IV) to give the 3-substituted 2-vinylphenyl sulfonate of the formula (I). Compounds of the formula (IV) are commercially available.

With preference in the method according to the invention, $R^1$ to $R^3$ are defined as follows:
$R^1$ is methyl, ethyl, n-propyl, isopropyl, n-butyl, phenyl, 4-methylphenyl or benzyl;
$R^2$ is Cl, F, Br, I or methyl; and
$R^3$ is F, Cl or $OSO_2R^1$.

With particular preference in the method according to the invention, $R^1$ to $R^3$ are defined as follows:
$R^1$ is methyl, ethyl, n-propyl, phenyl or 4-methylphenyl;
$R^2$ is Cl or Br; and
$R^3$ is F, Cl or $OSO_2R^1$.

With very particular preference in the method according to the invention, $R^1$ to $R^3$ are defined as follows:
$R^1$ is methyl or 4-methylphenyl, especially methyl;
$R^2$ is Cl or Br, especially Cl;
$R^3$ is F, Cl or $OSO_2R^1$.

At least one base is used in each of steps (a) and (b) of the method according to the invention. The bases used in steps (a) and (b) may be the same or different. With preference, the same base is used in steps (a) and (b).

With particular preference, the method according to the invention is carried out as a one-pot process, wherein the same base is used in steps (a) and (b). The base used in this case is added here at least in part, preferably completely, in step (a).

The total amount of base used in steps (a) and (b) is preferably 0.9 to 10 equivalents, particularly preferably 1.5 to 6.0 equivalents, especially preferably 3.0 to 5.0 equivalents, based in each case on one equivalent of the compound of the formula (II).

Suitable bases are one or more organic bases selected from the group consisting of trialkylamines such as trimethylamine, triethylamine, ethyldiisopropylamine, tri-n-propylamine and tri-n-butylamine; alkoxide bases such as potassiumtert-butoxide; pyridyl bases such as pyridine, 2,6-lutidine, 2-picoline, 3-picoline and 4-picoline; and amidine bases such as 1,8-diazabicyclo[5.4.0]undec-7-ene (DBU). Particular preference is given to tri-n-butylamine.

General Definitions

Halogen is F, Cl, Br or I, preferably Cl, Br or I, and particularly preferably Cl or Br.

$C_1$-$C_6$-alkyl is a saturated, branched or unbranched hydrocarbon radical having 1 to 6, preferably 1 to 3 carbon atoms, such as, for example, methyl, ethyl, n-propyl, isopropyl (1-methylethyl), n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Step (a)

In step (a), the compound of the formula (II) is reacted with an activator in the presence of a base to give the compound of the formula (III).

The activators used according to the invention are one or more compounds selected from the group consisting of thionyl chloride, phosgene, diphosgene, triphosgene, thiophosgene and chloroformic esters. Suitable chloroformic esters are $C_1$-$C_6$-alkyl chloroformates such as ethyl chloroformate and methyl chloroformate. Particularly preferred activators are thionyl chloride and phosgene, very particular preference being given to thionyl chloride.

The amount of activator used is preferably 0.8 to 2.5 equivalents, particularly preferably 0.9 to 2.0 equivalents and especially preferably 0.9 to 1.5 equivalents, based in each case on one equivalent of the compound of the formula (II).

The reaction is carried out in the presence of a base and a solvent.

Suitable bases are organic bases preferably selected from the group consisting of trialkylamines such as trimethylamine, triethylamine, ethyldiisopropylamine, tri-n-propylamine or tri-n-butylamine; alkoxide bases such as potassium tert-butoxide; pyridyl bases such as pyridine, 2,6-lutidine, 2-picoline, 3-picoline or 4-picoline; and amidine bases such as 1,8-diazabicyclo[5.4.0]undec-7-ene (DBU). Particular preference is given to tri-n-butylamine.

The amount of base used is preferably 0.9 to 5 equivalents, particularly preferably 2.0 to 3.5 equivalents, especially preferably 3.1 equivalents, based in each case on one equivalent of the compound of the formula (II).

Suitable solvents are aliphatic, alicyclic or aromatic hydrocarbons such as, for example, petroleum ether, n-hexane, n-heptane, cyclohexane, methylcyclohexane, toluene, o-xylene, m-xylene, p-xylene or decaline; halogenated hydrocarbons such as, for example, chlorobenzene, 1,2-dichlorobenzene, dichloromethane, chloroform, tetrachloromethane, dichloroethane or trichloroethane; ethers such as, for example, diethyl ether, diisopropyl ether, methyl tert-butyl ether (MTBE), methyl tert-amyl ether, 1,4-dioxane, tetrahydrofuran (THF), 2-methyltetrahydrofuran (2-Me-THF), 1,2-dimethoxyethane, 1,2-diethoxyethane, diglyme or anisole; nitriles such as, for example, acetonitrile, propionitrile, n-butyronitrile, isobutyronitrile or benzonitrile; ester solvents such as, for example, ethyl acetate; amide solvents such as, for example, N,N-dimethylformamide (DMF) or N,N-dimethylacetamide (DMAc); dipolar aprotic solvents such as, for example, dimethylsulfoxide (DMSO); or mixtures of these solvents. Particularly preferred solvents are toluene, acetonitrile, MTBE, THF and 2-Me-THF, and mixtures thereof. Very particular preference is given to toluene and MTBE.

The reaction in step (a) is preferably conducted at standard pressure, but can also be conducted at reduced or elevated pressure.

A solution comprising the compound of the formula (II), the base and the solvent is preferably initially charged and the activator is added with cooling, preferably at −20 to +10° C., preferably 0 to 5° C. The intermediate (V) is formed here.

The subsequent conversion of the intermediate (V) to give the compound of the formula (III) with elimination of O=X=Y is carried out preferably at a temperature of at least 0° C.:

When using a pyridyl base such as 3-picoline in combination with thionyl chloride as activator or when using thiophosgene as activator, the reaction temperature for the elimination is preferably at least 60° C., particularly preferably 80-120° C.

When using a trialkylamine base such as tributylamine in combination with thionyl chloride or phosgene as activator, the reaction temperature is preferably 0+25° C. This embodiment is therefore particularly advantageous.

The resulting reaction mixture comprising the compound of the formula (III) is preferably used in step (b) without work-up.

Step (b)

In step (b), the compound of the formula (III) is reacted in the presence of a base with the compound of the formula (IV) to give the 3-substituted 2-vinylphenyl sulfonate of the formula (I).

The amount of compound of the formula (IV) used is preferably 0.8 to 2.5 equivalents, particularly preferably 0.9 to 1.8 equivalents, especially preferably 1.0 to 1.5 equivalents, based in each case on one equivalent of the compound of the formula (III).

The reaction is carried out in the presence of a base and a solvent.

Suitable are those bases and solvents which have already been defined for step (a). The reaction is preferably carried out in the presence of the base used in step (a) and in the presence of the solvent used in step (a).

The amount of base used for step (b) is preferably already added in step (a), as described above, and is preferably 0.9 to 3.0 equivalents, particularly preferably 1.0 to 2.0 equivalents, especially preferably 1.1 to 1.5 equivalents, based in each case on one equivalent of the compound of the formula (II).

The reaction in step (b) is preferably conducted at standard pressure, but can also be conducted at reduced or elevated pressure.

The reaction temperature is preferably −20 to +100° C., particularly preferably −10 to +60° C., and especially preferably 0 to +30° C.

At the end of the reaction, the crude product is preferably first washed with aqueous acid and extracted, the combined organic phases are separated and the solvent is removed under reduced pressure. The product can be purified by recrystallization from, for example, ethanol.

In a particularly advantageous embodiment of the method according to the invention in which tri-n-butylamine is used as base, the tri-n-butylamine is recycled. For this purpose, the combined aqueous phases are preferably made alkaline by adding sodium hydroxide or potassium hydroxide and by removing the organic phase which separates out here, the tri-n-butylamine is recovered. The tri-n-butylamine may be purified by distillation.

Intermediate of the Formula (V)

The method according to the invention is characterized in that the conversion of the compound of the formula (II) in the presence of the activator and the base proceeds via the cyclic intermediate (V) to give the compound of the formula (III).

Therefore, the invention furthermore provides a compound of the formula (V),

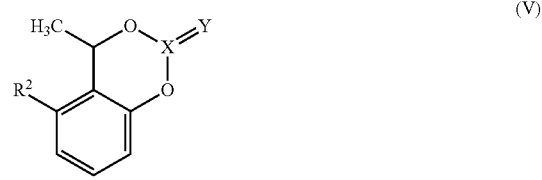

where X is C or S, Y is S or O, and X and Y cannot both be S (i.e. X≠Y); and $R^2$ is as defined in formula (II).

Particular preference is given to compounds of the formula (V) in which X is C and Y is S or O.

Very particular preference is given to compounds of the formula (V) in which X is S and Y is O.

Preparation of the Compound of the Formula (II)

The compound of the formula (II) may be obtained by reacting a compound of the formula (VI) or an alkali metal or alkaline earth metal salt of the compound of the formula (VI)

with at least one compound of the formula (VII)

in the presence of a solvent, where Q is Li, Na, K, MgCl, MgBr or MgI, and Me is methyl.

Preferably, Q is Li, MgCl, MgBr or MgI, and particularly preferably MgCl or MgBr.

In the case of the reaction of the compound of the formula (VI) with the organometallic compound of the formula (VII), the compound of the formula (VI) is both deprotonated and undergoes nucleophilic addition by the compound of the formula (VII), if the compound of the formula (VI) is not already present as the phenolate anion, for example in the form of an alkali metal or alkaline earth metal salt.

Preferred alkali metal salts are sodium and potassium salts. Preferred alkaline earth metal salts are magnesium or calcium salts.

The compound of the formula (VII) may serve both as deprotonating agent and as nucleophile for the addition reaction.

Variant i)

If one or more compounds of the formula (VII) are used both as deprotonating agent and as nucleophile, the total amount of compound of the formula (VII) used is preferably 1.8 to 4.0 equivalents, particularly preferably 2.0 to 2.5 equivalents, based in each case on 1 equivalent of the compound of the formula (VI).

Variant ii)

Preferably, however, a deprotonating agent is used which is not a compound of the formula (VII). In this embodiment, the compound of the formula (VI) is first treated with the deprotonating agent in the presence of a solvent before it is reacted with the compound of the formula (VII).

Suitable deprotonating agents are alkali metal alkoxides and alkali metal hydroxides, preferably selected from the group consisting of sodium hydroxide, potassium hydroxide, sodium methoxide, sodium ethoxide, sodium tert-butoxide, potassium methoxide and potassium tert-butoxide.

If a deprotonating agent is used, this is preferably added at a reaction temperature of 0 to +100° C., particularly preferably 20 to +80° C., and especially preferably 40 to +80° C.

Suitable as solvent for the deprotonation are ethers such as THF, Me-THF, dioxane, MTBE or anisole, alcohols such as methanol or ethanol and aromatic hydrocarbons such as toluene, xylene, chlorobenzene or 1,2-dichlorobenzene. Particular preference is given to THF, MTBE or toluene in combination with a solution of sodium methoxide in methanol.

Water and protic solvents such as alcohols must be removed before the deprotonated compound of the formula (VI) is reacted with the organometallic compound of the formula (VII). In the case of water, this is preferably removed by azeotropic distillation with toluene for example. In the case of alcohols such as methanol or ethanol, the removal may be effected by distillation in the presence of a higher-boiling solvent such as, for example, toluene.

By using the deprotonating agent, the amount of compound of the formula (VII) used may be reduced. For instance, when using a deprotonating agent, preferably at most 1.8 equivalents, particularly preferably at most 1.5 equivalents, and especially preferably 0.9 to 1.2 equivalents of compound of the formula (VII) are used, based in each case on 1 equivalent of the compound of the formula (VI).

Suitable as solvent for the addition of the organometallic reagent (VII) are aliphatic, alicyclic or aromatic hydrocarbons such as, for example, petroleum ether, n-hexane, n-heptane, cyclohexane, methylcyclohexane, toluene, o-xylene, m-xylene, p-xylene or decaline; ethers such as, for example, diethyl ether, diisopropyl ether, methyl tert-butyl ether (MTBE), methyl tert-amyl ether, 1,4-dioxane, tetrahydrofuran (THF), 2-methyltetrahydrofuran (2-Me-THF), 1,2-dimethoxyethane, 1,2-diethoxyethane or anisole; and mixtures of these solvents. Particularly preferred solvents are toluene, o-xylene, m-xylene, p-xylene, n-hexane, cyclohexane, methylcyclohexane, MTBE, THF or 2-Me-THF, and mixtures thereof. Very particular preference is given to THF, 2-Me-THF, MTBE, toluene, o-xylene, m-xylene, p-xylene and mixtures thereof.

Preparation of the Compound of the Formula (VI)

The compound of the formula (VI), in which $R^2$ is Cl, may be obtained by reacting a compound of the formula (VIII)

(VIII)

where $R^2$ is Cl, with a hydroxide base in the presence of a solvent.

This synthesis of the compound of the formula (VI) is known in principle from WO 2012/087229. The reaction is described therein using KOH in DMSO as solvent. However, DMSO is an unsuitable solvent for industrial use and the yield described is moderate.

Suitable as hydroxide base in the method according to the invention are alkali metal hydroxides, in particular sodium hydroxide and potassium hydroxide. Particular preference is given to aqueous alkali metal hydroxide solutions, particularly potassium hydroxide solutions and aqueous sodium hydroxide solutions.

Suitable solvents are amide solvents such as, e.g. N,N-dimethylformamide (DMF) and N,N-dimethylacetamide (DMAc); diglyme; mixtures of these solvents and also solvent mixtures of amide solvents or diglyme with aromatic solvents such as, e.g. toluene, xylene (o-xylene, p-xylene and/or m-xylene), chlorobenzene and 1,2-dichlorobenzene, or ether solvents such as THF, Me-THF and dioxane.

Preference is given to using diglyme or an amide solvent selected from DMF and DMAc.

Particular preference is given to using DMAc.

Very particular preference is given to using a combination of aqueous potassium hydroxide solution as hydroxide base and N,N-dimethylacetamide as solvent.

The preferred synthesis of the compound of the formula (II) in accordance with the invention, starting from the compound of the formula (VIII) via the compound of the formula (VI), is shown in scheme 2, where $R^2$ is Cl in each case:

Scheme 2

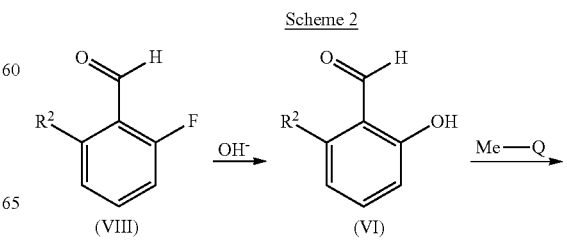

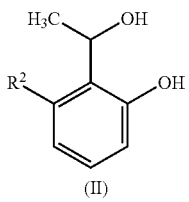

(II)

EXAMPLES

The present invention is elucidated in more detail by the examples which follow, without restricting the invention to these examples.

Example 1

2-Chloro-6-hydroxybenzaldehyde (VI, $R^2$=Cl)

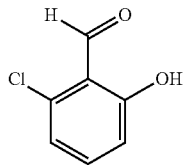

In a 500 ml 4-neck flask, a solution of 50.0 g (0.31 mol, 1.0 eq) of 2-chloro-6-fluorobenzaldehyde in 150 ml of N,N-dimethylacetamide is initially charged at 23° C. under nitrogen. 87.6 g (0.78 mol, 2.5 eq) of 50% aqueous KOH solution is metered in at 20-30° C. over 3 h. The reaction is slightly exothermic and a yellow suspension is obtained. After the addition had ended, the reaction mixture is stirred at 23° C. for a further 1 h. GC shows >99% conversion. With cooling at 10-30° C., 200 ml of water and then 80.0 g of 37% HCl are metered in over 10-20 min (pH=1-2). A beige solid precipitates out.

Optionally, this solid may be isolated by filtration. After drying at 20 mbar/23° C., 43.0 g of a beige-coloured solid are obtained (88% yield).

Alternatively, 150 ml of toluene are added and the mixture is stirred at 23° C. for 10 minutes. The aqueous phase is separated and extracted again with 150 ml of toluene. The combined organic phases are washed with 150 ml of 10% HCl and concentrated on a rotary evaporator at 40° C./50 mbar to ca. 250 g. The product solution is used as such in the next step (calculated yield by content determination by means of quant. NMR: 90%).

$^1$H-NMR (CDCl$_3$, 400 MHz) δ (ppm)=11.91 (s, 1H), 10.42 (s, 1H), 7.42 (t, J=8.3 Hz, 1H), 6.96 (dd, J=8.0 Hz, 1.0 Hz, 1H), 6.90 (d, J=8.4 Hz, 1H).

Example 2

3-Chloro-2-(1-hydroxyethyl)phenol (II, $R^2$=Cl)

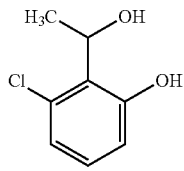

In a 1 L 4-neck flask, the product solution from example 1 consisting of 43.8 g (0.28 mol, 1.0 eq) of 2-chloro-6-hydroxybenzaldehyde in toluene (90% determined yield) is initially charged under nitrogen and heated to 60° C. 50.3 g (0.28 mol, 1.0 eq) of 30% sodium methoxide solution in methanol is metered in at 60° C. over 1 h and, after the addition is complete, the mixture is further stirred at 60° C. for 2 h. The yellow suspension is cooled to 23° C., 300 ml of toluene are added and the mixture is concentrated on a rotary evaporator at 40° C./50 mbar down to a residual weight of ca. 250 g. 105.4 g (0.31 mol, 1.1 eq) of 22% methylmagnesium chloride solution in THF is metered in at 20-30° C. over 3 h and the mixture further stirred at 23° C. for 1 h. HPLC shows complete conversion. With cooling at 10-20° C., 250 ml of 10% HCl (pH=1-2) is metered in over 30 minutes. The aqueous phase is separated and extracted with 200 ml of toluene. The combined organic phases are washed with 100 ml of 10% NaHCO$_3$ solution. The organic phase is separated, washed with 100 ml of water and concentrated on a rotary evaporator at 40° C./50 mbar down to a residual weight of ca. 200 g. The product solution is used in the next step (calculated yield by content determination by means of quant. NMR: 98%).

$^1$H-NMR (CDCl$_3$, 400 MHz) δ (ppm)=8.84 (s, 1H), 7.07 (t, J=8.0 Hz, 1H), 6.85 (dd, J=8.0 Hz, 1.2 Hz, 1H), 6.78 (dd, J=8.3 Hz, 1.1 Hz, 1H), 5.60 (qd, J=6.5 Hz, 3.1 Hz, 1H), 2.65 (m, 1H), 1.57 (d, J=6.5 Hz, 3H).

Examples 3-6

In analogy to the method description of example 2 for the preparation of the compound of the formula (II) where $R^2$=Cl, the compounds of the formula (II) of examples 3-6 below may be obtained:

Example 3: 3-Fluoro-2-(1-hydroxyethyl)phenol (II, $R^2$=F)

$^1$H-NMR (CDCl$_3$, 400 MHz) δ (ppm)=8.59 (br s, 1H), 7.08 (dt, J=8.3 Hz, 6.5 Hz, 1H), 6.65 (d, J=8.3 Hz, 1H), 6.58-6.51 (m, 1H), 5.48 (q, J=6.5 Hz, 1H), 2.69 (br s, 1H), 1.58 (d, J=6.7 Hz, 3H).

Example 4: 2-(1-Hydroxyethyl)-3-iodophenol (II, $R^2$=I)

$^1$H-NMR (CDCl$_3$, 400 MHz) δ (ppm)=8.88 (br s, 1H), 7.33 (dd, J=7.5 Hz, 1.6 Hz, 1H), 6.88-6.80 (m, 2H), 5.38 (q, J=6.7 Hz, 1H), 2.80 (br s, 1H), 1.54 (d, J=6.7 Hz, 3H).

Example 5: 3-Bromo-2-(1-hydroxyethyl)phenol (II, $R^2$=Br)

$^1$H-NMR (CDCl$_3$, 400 MHz) δ (ppm)=9.02 (br s, 1H), 7.04 (dd, J=8.0 Hz, 1.1 Hz, 1H), 6.99 (t, J=8.0 Hz, 1H), 6.82 (dd, J=8.0 Hz, 1.3 Hz, 1H), 5.53 (q, J=6.7 Hz, 1H), 3.25 (br s, 1H), 1.56 (d, J=6.7 Hz, 3H).

Example 6: 2-(1-Hydroxyethyl)-3-methylphenol (II, $R^2$=Me)

$^1$H-NMR (CDCl$_3$, 400 MHz) δ (ppm)=8.61 (br s, 1H), 7.04 (t, J=8.0 Hz, 1H), 6.73 (d, J=8.0 Hz, 1H), 6.65 (d, J=7.5 Hz, 1H), 5.33 (q, J=6.7 Hz, 1H), 2.92 (br s, 1H), 2.22 (s, 3H), 1.54 (d, J=6.7 Hz, 3H).

Example 7

3-Chloro-2-vinylphenyl methanesulfonate (I, $R^1$=Me, $R^2$=Cl)

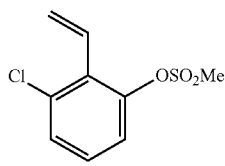

Stage a) 3-Chloro-2-vinylphenol (III, $R^2$=Cl)

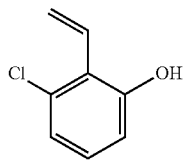

In a 1 L 4-neck flask, the product solution from example 2 consisting of 46.6 g (0.27 mol, 1.0 eq) of 3-chloro-2-(1-hydroxyethyl)phenol in toluene (98% determined yield) and 222.3 g (1.2 mol, 4.5 eq) of tributylamine are initially charged under nitrogen and a solution consisting of 35.7 g (0.30 mol, 1.1 eq) of thionyl chloride in 30 ml of toluene at 0-5° C. is metered in over a period of 2 h. After the addition has ended, the reaction mixture is stirred at 23° C. for 1 h. HPLC shows >98% conversion to the styrene. Analytical data for 3-chloro-2-vinylphenol (III, $R^2$=Cl) are as follows: $^1$H-NMR (CDCl$_3$, 400 MHz) δ (ppm)=7.08 (dd, J=8.0, 8.0 Hz, 1H), 6.96 (d, J=8.0 Hz, 1H), 6.84 (d, J=8.0 Hz, 1H), 6.79 (dd, J=12.0, 12.0 Hz, 1H), 5.74 (d, J=12.0 Hz, 1H), 5.73 (s, 1H), 5.68 (d, J=12.0 Hz, 1H).

The cyclic intermediate, 5-chloro-4-methyl-4H-1,3,2-benzodioxathiin 2-oxide (V, $R^2$=Cl, X=S, Y=O), cannot be isolated or be detected by diverse analytical methods. The hydrolyzed derivative 1-(2-chloro-6-hydroxyphenyl)ethyl hydrogensulfite, ring-opened by water, can be detected in very low amounts (<5%) during the reaction by LC-MS. Analytical data for 1-(2-chloro-6-hydroxyphenyl)ethyl hydrogensulfite are as follows: ESI neg. m/z=235 [M−H]$^+$; retention time: 1.18 min (HPLC column: Phenomenex Kinetex C18, 100 mm×2.1 mm×1.7 µl, eluent A: 0.1% formic acid/water, eluent B: acetonitrile, gradient: 90/10 (0 min) →18/82 (2.4 min)→0/100 (2.6 min)→0/100 (3.59 min), flow rate: 0.8 ml/min, oven: 40° C., inj.: 1.0 µl).

Stage b) 3-Chloro-2-vinylphenyl methanesulfonate (I, $R^1$=Me, $R^2$=Cl)

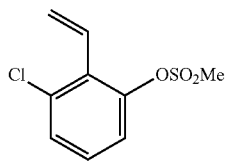

Then, at 0-5° C., 36.6 g (0.32 mol, 1.2 eq) of methanesulfonyl chloride are metered in over 2 h. After the addition is complete, the reaction mixture is stirred at 23° C. for 1 h. HPLC shows >98% conversion to the methanesulfonate. The reaction mixture is metered into 350 ml of 10% HCl at 0-10° C. over 1 h and the aqueous phase is then extracted twice with 200 ml of toluene each time. The combined organic phases are washed with 150 ml of 10% HCl and concentrated on a rotary evaporator at 40° C./50 mbar. The oily residue is taken up in 50 ml of DMAc and at 15-25° C. is metered into a mixture of 125 ml of 37% HCl and 500 ml of water over 1 h. The beige coloured solid is filtered off with suction and washed with 200 ml of water. After drying at 35° C./20 mbar, 63.7 g of a beige coloured solid is obtained (88% yield; 78% yield over all stages; 88% purity according to quant. HPLC).

By recrystallization from 30 g of ethanol, 51.2 g of colourless crystals are obtained (80% yield; 70% yield over all stages; >98% purity according to quant. HPLC).

$^1$H-NMR (CDCl$_3$, 400 MHz) δ (ppm)=7.36 (dd, J=8.0, 1.2 Hz, 1H), 7.34 (dd, J=8.0, 1.2 Hz, 1H), 7.23 (t, J=8.0 Hz, 1H), 6.76 (dd, J=18.0 Hz, 11.7 Hz, 1H), 5.91 (dd, J=18.0, 1.6 Hz, 1H), 5.73 (dd, J=11.8, 1.4 Hz, 1H), 3.11 (s, 3H).

Example 8

3-Chloro-2-vinylphenyl Methanesulfonate (I, $R^1$=Me, $R^2$=Cl): Variant with Isolated Yield Over the Latter Two Stages and Recycling of Tri-n-Butylamine Stage a) 3-Chloro-2-vinylphenol (III, $R^2$=Cl)

In a 250 ml 4-neck flask, a solution of 10.0 g (57.9 mmol, 1.0 eq) of 3-chloro-2-(1-hydroxyethyl)phenol and 48.3 g of tri-n-butylamine (260.7 mmol, 4.5 eq) in 50 ml of methyl tert-butyl ether is initially charged under nitrogen and 7.6 g (63.7 mmol, 1.1 eq) of thionyl chloride at 0-5° C. are metered in over a period of 1 h. After the addition is complete, the reaction mixture is stirred at 23° C. for 1 h. HPLC shows >98% conversion to the styrene. Analytical data for 3-chloro-2-vinylphenol (III, $R^2$=Cl) are as follows: $^1$H-NMR (CDCl$_3$, 400 MHz) δ (ppm)=7.08 (dd, J=8.0, 8.0 Hz, 1H), 6.96 (d, J=8.0 Hz, 1H), 6.84 (d, J=8.0 Hz, 1H), 6.79 (dd, J=12.0, 12.0 Hz, 1H), 5.74 (d, J=12.0 Hz, 1H), 5.73 (s, 1H), 5.68 (d, J=12.0 Hz, 1H).

Stage b) 3-Chloro-2-vinylphenyl methanesulfonate (I, $R^1$=Me, $R^2$=Cl)

Then, at 0-5° C., 8.0 g (69.5 mmol, 1.2 eq) of methanesulfonyl chloride are metered in over 1 h. After the addition is complete, the reaction mixture is stirred at 23° C. for 1 h. HPLC shows >98% conversion to the methanesulfonate. 100 ml of 10% HCl are metered in to the reaction mixture at 10-15° C. and the phases are subsequently separated. The aqueous phase is extracted twice with 100 ml of methyl tert-butyl ether each time. The combined organic phases are washed twice with 50 ml of 10% HCl each time, dried over MgSO4 and concentrated on a rotary evaporator at 40° C./10 mbar (13.9 g; purity according to quant. HPLC: 83%; 86% yield). The material thus obtained is recrystallized from ethanol/n-heptane (10.8 g; purity by quant. HPLC: 99%; 80% yield).

The aqueous phase is brought to a pH of 11-12 by addition of 50% NaOH. The organic phase that separates out is separated off and is distilled over on the rotary evaporator at 90° C./10 mbar.

A colourless liquid is obtained, which can be identified as tri-n-butylamine by comparison with literature data (1H-NMR) (43.6 g; 90% recovery).

Examples 9-13

In analogy to the method descriptions of examples 7 and 8, the following specified compounds of the formula (III) or (I) may be obtained:

Example 9: 3-Bromo-2-vinylphenol (III, $R^2$=Br)

$^1$H-NMR (CDCl$_3$, 400 MHz) δ (ppm)=7.13 (dd, J=7.8, 1.3 Hz, 1H), 7.00 (t, J=7.8 Hz, 1H), 6.94 (dd, J=8.0, 1.3 Hz, 1H), 6.74 (dd, J=18.1 Hz, 11.4 Hz, 1H), 5.72 (dd, J=18.1, 1.6 Hz, 1H), 5.70 (dd, J=11.4, 1.6 Hz, 1H).

Example 10: 3-Bromo-2-vinylphenyl Methanesulfonate (I, $R^1$=Me, $R^2$=Br)

$^1$H-NMR (CDCl$_3$, 600 MHz) δ (ppm)=7.56 (dd, J=8.1, 1.1 Hz, 1H), 7.38 (d, J=8.2 Hz, 1H), 7.16 (t, J=8.1 Hz, 1H), 6.72 (dd, J=17.9 Hz, 11.7 Hz, 1H), 5.84 (dd, J=17.9, 1.3 Hz, 1H), 5.71 (dd, J=11.7, 1.3 Hz, 1H), 3.11 (s, 3H).

Example 11: 3-Fluoro-2-vinylphenyl Methanesulfonate (I, $R^1$=Me, $R^2$=F)

$^1$H-NMR (CDCl$_3$, 400 MHz) δ (ppm)=7.27-7.24 (m, 1H), 7.23-7.19 (m, 1H), 7.10-7.04 (m, 1H), 6.75 (dd, J=18.0 Hz, 11.9 Hz, 1H), 6.06 (dd, J=18.0, 1.3 Hz, 1H), 5.68 (dd, J=11.9, 1.6 Hz, 1H), 3.15 (s, 3H).

Example 12: 3-Iodo-2-vinylphenyl Methanesulfonate (I, $R^1$=Me, $R^2$=I)

$^1$H-NMR (CDCl$_3$, 400 MHz) δ (ppm)=7.84 (dd, J=8.1 Hz, 1.1 Hz, 1H), 7.41 (dd, J=8.1 Hz, 1.1 Hz, 1H), 7.00 (t, J=8.0 Hz, 1H), 6.60 (dd, J=17.8 Hz, 11.6 Hz, 1H), 5.72 (dd, J=17.8, 1.4 Hz, 1H), 5.67 (dd, J=11.6, 1.4 Hz, 1H), 3.11 (s, 3H).

Example 13: 3-Methyl-2-vinylphenyl Methanesulfonate (I, $R^1$=Me, $R^2$=Me)

$^1$H-NMR (CDCl$_3$, 400 MHz) δ (ppm)=7.24 (dd, J=8.0, 1.8 Hz, 1H), 7.19 (t, J=7.8 Hz, 1H), 7.15 (dd, J=7.5, 1.3 Hz, 1H), 6.71 (dd, J=17.8 Hz, 11.8 Hz, 1H), 5.66 (dd, J=11.8, 1.8 Hz, 1H), 5.63 (dd, J=17.8, 1.8 Hz, 1H), 3.09 (s, 3H), 2.37 (s, 3H).

Example 14

Alternative Conditions for the Preparation of 3-chloro-2-vinylphenol (III, $R^2$=Cl) from 3-chloro-2-(1-hydroxyethyl)phenol (II, $R^2$=Cl)

a) 3-Picoline as Base 1.0 g of 3-chloro-2-(1-hydroxyethyl)phenol (5.8 mmol, 1.0 eq) are initially charged in 9 ml of DMAc and 2.43 g of 3-picoline (26.1 mmol, 4.5 eq) are added. 0.76 g of thionyl chloride (6.4 mmol, 1.1 eq) are metered in at 0-5° C. over 1 h and the mixture is then stirred at 23° C. for 1 h. HPLC shows >95% conversion to 3-chloro-2-[1-(3-methylpyridinium-1-yl)ethyl]phenolate. Analytical data for 3-chloro-2-[1-(3-methylpyridinium-1-yl)ethyl] phenolate are as follows: ESI pos. m/z=248 [M+H]$^+$; $^1$H-NMR (CDCl$_3$, 400 MHz) δ (ppm)=8.88 (d, J=6.2 Hz, 1H), 8.73 (s, 1H), 8.25 (d, J=8.0 Hz, 1H), 7.95 (t, J=6.2 Hz, 1H), 7.59 (dd, J=8.4 Hz, 1.0 Hz, 1H), 7.14 (t, J=8.3 Hz, 1H), 6.89 (dd, J=8.0 Hz, 1.1 Hz, 1H), 6.46 (q, J=7.0 Hz, 1H), 2.59 (s, 3H), 2.22 (d, J=7.0 Hz, 3H).

The reaction mixture is then heated to 120° C. and stirred at this temperature for 2 h. HPLC shows >85% 3-chloro-2-vinylphenol (III, $R^2$=Cl, analytical data: see examples 7 and 8, stage a).

b) Phosgene as Activator (with Conversion of Intermediate (V) to the Compound (III) at 110° C.)

5.0 g of 3-chloro-2-(1-hydroxyethyl)phenol (29.0 mmol, 1.0 eq) are initially charged in 50 ml of toluene and 21.5 g of tributylamine (115.9 mmol, 4.0 eq) are added. At 0-5° C., 5.8 g of phosgene (58.0 mmol, 2.0 eq) are introduced over 1 h and the mixture is then stirred at 23° C. for 1 h. HPLC-MS shows >80% 5-chloro-4-methyl-4H-1,3-benzodioxin-2-one (V, $R^2$=Cl, X=C, Y=O) as intermediate. Analytical data for 5-chloro-4-methyl-4H-1,3-benzodioxin-2-one (V, $R^2$=Cl, X=C, Y=O) are as follows: ESI pos. m/z=199 [M+H]$^+$; retention time: 1.02 min (HPLC column: Zorbax Eclipse Plus C18, 50 mm×2.1 mm×1.8 µl; eluent A: 0.1% formic acid/acetonitrile; eluent B: 0.1% formic acid/water; gradient: 10/90 47%/min→95/5 (0.7 min); flow rate: 1 ml/min; oven: 55° C.; injection: 0.8 µl).

The reaction mixture is then heated to 110° C. and stirred at this temperature for 12 h. HPLC shows >90% 3-chloro-2-vinylphenol (III, $R^2$=Cl, analytical data see examples 7 and 8, stage a).

b) Phosgene as Activator (with Conversion of Intermediate (V) to the Compound (III) at Room Temperature)

10.0 g of 3-chloro-2-(1-hydroxyethyl)phenol (57.9 mmol, 1.0 eq) are initially charged in 50 ml of toluene and 43 g of tributylamine (231 mmol, 4.0 eq) are added. At 0-6° C., 8.6 g of phosgene (86.9 mmol, 1.5 eq) are introduced over 30 min and the mixture is then stirred at 0° C. for 1 h. HPLC-MS shows 80% 5-chloro-4-methyl-4H-1,3-benzodioxin-2-one (V, $R^2$=Cl, X=C, Y=O) as intermediate. Analytical data for 5-chloro-4-methyl-4H-1,3-benzodioxin-2-one (V, $R^2$=Cl, X=C, Y=O) are as follows: ESI pos. m/z=199 [M+H]$^+$; retention time: 1.02 min (HPLC column: Zorbax Eclipse Plus C18, 50 mm×2.1 mm×1.8 µl; eluent A: 0.1% formic acid/acetonitrile; eluent B: 0.1% formic acid/water; gradient: 10/90 47%/min→95/5 (0.7 min); flow rate: 1 ml/min; oven: 55° C.; injection: 0.8 µl).

The reaction mixture is then brought to room temperature and excess phosgene is driven off by introducing an argon gas stream. 50 ml of methanol are then added at room temperature and the mixture is stirred for 1 h. LCMS shows >80% 3-chloro-2-vinylphenol. The mixture is set to pH 10-11 with dilute NaOH, the phases are separated and the organic phase is extracted again 2× with dilute NaOH. The aqueous phases are combined, set to pH 2 with dilute HCl and extracted 3× with ethyl acetate. The combined organic phase is dried over sodium sulfate and concentrated on the rotary evaporator. This gives 7.9 g of 3-chloro-2-vinylphenol (III, $R^2$=Cl, analytical data see examples 7 and 8, stage a) at a purity of 87% (yield: 76.7% of theory) as a yellow oil.

d) Thiophosgene as Activator (with Isolation and Characterization of the Intermediate (V))

1.0 g of 3-chloro-2-(1-hydroxyethyl)phenol (5.8 mmol, 1.0 eq) is initially charged in 5 ml of MTBE and 2.15 g of tri-n-butylamine (11.6 mmol, 2.0 eq) are added. 0.76 g of thiophosgene (6.4 mmol, 1.1 eq) are metered in at 0-50° C. over 1 h and the mixture is then stirred at 23° C. for 1 h. HPLC shows >80% 5-chloro-4-methyl-4H-1,3-benzodioxin-2-thione (V, $R^2$=Cl, X=C, Y=S) as intermediate. Ca.

1 ml of the reaction solution is withdrawn and worked-up on a small scale by washing with 10% HCl. The organic phase is then concentrated on the rotary evaporator. Analytical data for 5-chloro-4-methyl-4H-1,3-benzodioxin-2-thione (V, $R^2$=Cl, X=C, Y=S) are as follows: CI m/z=215 [M+H]$^+$; $^1$H-NMR (CDCl$_3$, 400 MHz) δ (ppm)=7.35 (t, J=8.3 Hz, 1H), 7.27 (dd, J=8.0 Hz, 1.1 Hz, 1H), 7.11 (dd, J=8.3 Hz, 0.8 Hz, 1H), 5.75 (q, J=6.7 Hz, 3.1 Hz, 1H), 1.72 (d, J=6.7 Hz, 3H).

1.61 g of tri-n-butylamine (8.7 mmol, 1.5 eq) are added to the remaining reaction mixture which is then heated to 80° C. HPLC shows >80% conversion to 3-chloro-2-vinylphenol (III, $R^2$=Cl, analytical data: see examples 7 and 8, stage a).

The invention claimed is:

1. Method for preparing a vinylphenyl sulfonate of formula (I):

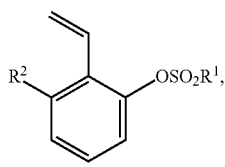

in which $R^1$ is $C_1$-$C_6$-alkyl, phenyl, 4-methylphenyl or benzyl, and
$R^2$ is halogen or methyl,
comprising reacting
(a) a compound of formula (II)

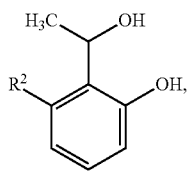

with an activator in the presence of a base to give a compound of formula (III)

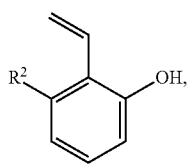

wherein one or more compounds are used as activators selected from the group consisting of thionyl chloride, phosgene, diphosgene, triphosgene, thiophosgene and chloroformic esters,
and reacting
(b) the compound of the formula (III) in the presence of a base with a compound of formula (IV)

$$R^1-SO_2-R^3 \quad (IV),$$

where $R^3$ is F, Cl, Br or $OSO_2R^1$ and $R^1$ is as defined in formula (I),
to give the vinylphenyl sulfonate of the formula (I).

2. Method according to claim 1, wherein a) and b) are carried out in a one-pot process.

3. Method according to claim 1, wherein one or more bases selected from the group consisting of trialkylamines, pyridyl bases, alkoxide bases and amidine bases is used in (a) and (b).

4. Method according to claim 3, wherein the base used is tributylamine.

5. Method according to claim 1, wherein one or more solvents are used in (a) and (b) selected from the group consisting of petroleum ether, n-hexane, n-heptane, cyclohexane, methylcyclohexane, toluene, o-xylene, m-xylene, p-xylene, decaline, chlorobenzene, 1,2-dichlorobenzene, dichloromethane, chloroform, tetrachloromethane, dichloroethane, trichloroethane, diethyl ether, diisopropyl ether, methyl tert-butyl ether, methyl tert-amyl ether, 1,4-dioxane, tetrahydrofuran, 2-methyltetrahydrofuran, 1,2-dimethoxyethane, 1,2-diethoxyethane, diglyme, anisole, acetonitrile, propionitrile, n-butyronitrile, isobutyronitrile, benzonitrile, ethyl acetate, N,N-dimethylformamide, N,N-dimethylacetamide, dimethylsulfoxide.

6. Method according to claim 1, wherein the solvent used is toluene or methyl tert-butyl ether.

7. Method according to claim 1, wherein
$R^1$ is methyl, ethyl, n-propyl, isopropyl, n-butyl, phenyl, 4-methylphenyl or benzyl,
$R^2$ is Cl, F, Br, I or methyl, and
$R^3$ is F, Cl or $OSO_2R^1$.

8. Method according to claim 1, wherein the compound of the formula (II) is obtained by reacting a compound of the formula (VI) or an alkali metal salt or alkaline earth metal salt of the compound of formula (VI)

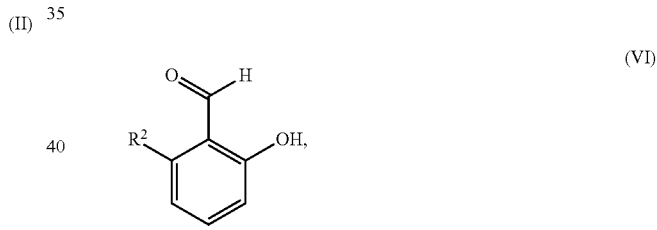

with at least one compound of formula (VII)

$$Me-Q \quad (VII)$$

in the presence of a solvent, where Q is Li, Na, K, MgCl, MgBr or MgI.

9. Method according to claim 8, wherein a deprotonating agent is first added to the compound of the formula (VI) before reacting with the compound of the formula (VII), wherein the deprotonating agent is not a compound of the formula (VII).

10. Method according to claim 9, wherein an alkali metal alkoxide and/or alkali metal hydroxide is used as deprotonating agent.

11. Method according to claim 10, wherein the deprotonating agent is selected from the group consisting of sodium hydroxide, potassium hydroxide, sodium methoxide, sodium ethoxide, sodium tert-butoxide, potassium methoxide and potassium tert-butoxide.

12. Method according to claim 8, wherein the compound of the formula (VI) is obtained by reacting a compound of formula (VIII)

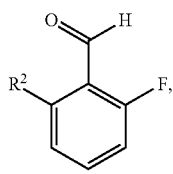

(VIII)

where R² is methyl, I, Br or Cl,
with a hydroxide base.

13. Method according to claim 12, wherein the hydroxide base used is an aqueous potassium hydroxide solution or an aqueous sodium hydroxide solution.

14. Method according to claim 12, wherein the reaction of the compound of the formula (VIII) to the compound of the formula (VI) is carried out in the presence of an amide solvent, or a mixture of amide solvent or diglyme with ether solvent or aromatic solvent.

15. Compound of formula (V),

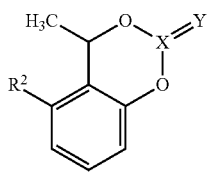

(V)

in which R² is halogen or methyl;
X is C or S, Y is S or O, and wherein X and Y cannot both be S.

* * * * *